(12) United States Patent
Tinkham et al.

(10) Patent No.: US 11,607,115 B2
(45) Date of Patent: Mar. 21, 2023

(54) ENDOSCOPIC ULTRASOUND FINE NEEDLE ASPIRATION DEVICE

(71) Applicant: BOSTON SCIENTIFIC SCIMED, INC., Maple Grove, MN (US)

(72) Inventors: Brian Tinkham, Scituate, MA (US); Robert DeVries, Northborough, MA (US); Michal Weisman, Winchester, MA (US); Shawn Ryan, Littleton, MA (US); Daniel Bacon, Fitchburg, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 1291 days.

(21) Appl. No.: 15/702,463

(22) Filed: Sep. 12, 2017

(65) Prior Publication Data
US 2018/0008127 A1    Jan. 11, 2018

Related U.S. Application Data

(63) Continuation of application No. 13/226,183, filed on Sep. 6, 2011, now Pat. No. 9,788,707.
(Continued)

(51) Int. Cl.
*A61B 1/00*      (2006.01)
*A61B 1/018*     (2006.01)
(Continued)

(52) U.S. Cl.
CPC ...... *A61B 1/00131* (2013.01); *A61B 1/00066* (2013.01); *A61B 1/00128* (2013.01);
(Continued)

(58) Field of Classification Search
CPC ............... A61B 10/04; A61B 10/0283; A61B 2010/045; A61B 1/018; A61B 17/3478; A61B 2010/0208; A61B 10/0233
See application file for complete search history.

(56) References Cited

U.S. PATENT DOCUMENTS 9,895,142 B2 *  2/2018  Sato .................. A61B 17/00234
2005/0228312 A1 * 10/2005  Surti ................... A61B 10/0283
                                                            600/567

FOREIGN PATENT DOCUMENTS

WO      2008/078499      7/2008

* cited by examiner

*Primary Examiner* — Alexandra L Newton
(74) *Attorney, Agent, or Firm* — Fay Kaplun & Marcin, LLP

(57) ABSTRACT

A handle for a medical device includes a proximal segment defining a proximal lumen extending therethrough and sized and shaped to receive an endoscopic medical device therein. A medial segment is received within a distal portion of the proximal segment and has an outer diameter smaller than an inner diameter thereof. A medial lumen extends through the proximal segment and is open to the proximal lumen. A distal segment is received within a distal portion of the medial segment and defines a distal lumen extending therethrough open to the medial lumen. The distal segment has an outer diameter smaller than an inner diameter of the medial segment. The medial segment includes a first movement limiting mechanism limiting movement of an endoscopic medical device inserted therethrough along an axis of the distal lumen and a second movement limiting mechanism limiting advancement of an endoscope attached to the distal body portion.

18 Claims, 3 Drawing Sheets

Related U.S. Application Data

(60) Provisional application No. 61/380,471, filed on Sep. 7, 2010.

(51) Int. Cl.
*A61B 10/04* (2006.01)
*A61B 10/02* (2006.01)
*A61B 17/00* (2006.01)
*A61B 90/00* (2016.01)

(52) U.S. Cl.
CPC .............. *A61B 1/018* (2013.01); *A61B 10/04* (2013.01); *A61B 10/0283* (2013.01); *A61B 2010/045* (2013.01); *A61B 2017/0034* (2013.01); *A61B 2017/00292* (2013.01); *A61B 2090/034* (2016.02); *A61B 2090/062* (2016.02); *A61B 2090/0811* (2016.02)

ENDOSCOPIC ULTRASOUND FINE NEEDLE ASPIRATION DEVICE

PRIORITY CLAIM

The present application is a Continuation of U.S. patent application Ser. No. 13/226,183 filed on Sep. 6, 2011, now U.S. Pat. No. 9,788,707, which claims priority to U.S. Provisional Application Ser. No. 61/380,471, entitled "Endoscopic Ultrasound Fine Needle Aspiration Device," filed on Sep. 7, 2010. The entire disclosure of the above patents/applications is expressly incorporated herein by reference.

BACKGROUND may be performed with Endoscopic Ultrasound Fine Needle Aspiration ("EUS-FNA") devices to obtain cells or small samples of tissue from, for example, the breast or liver for cytology studies, endoscopy or oncology. As understood by those skilled in the art, biopsy needles enable the capture of samples to facilitate diagnosis and treatment. These biopsy needles are generally connected at their proximal ends to handles including actuation mechanisms. Currently available handles are typically formed as two or more overlapping substantially cylindrical elements with a first element attached to an endoscope and a second larger diameter element overlapping a proximal portion of the first element being used to advance the needle to a target site in a living body. Presently available handles and actuation mechanisms offer insufficient ergonomics and further require that the entire handle be rotated to rotate the needle attached thereto.

SUMMARY OF THE INVENTION

The present invention relates to a handle for a medical device comprising a proximal segment defining a proximal lumen extending longitudinally therethrough, the proximal lumen being sized and shaped to receive an endoscopic medical device therein and a medial segment received within a distal portion of the proximal segment, the medial segment having an outer diameter smaller than an inner diameter of the proximal segment and defining a medial lumen extending therethrough open to the proximal lumen in combination with a distal segment received within a distal portion of the medial segment and defining a distal lumen extending therethrough open to the medial lumen, the distal segment having an outer diameter smaller than an inner diameter of the medial segment, wherein the medial segment includes a first movement limiting mechanism limiting movement of an endoscopic medical device inserted through the proximal, medial and distal lumens along an axis of the distal lumen and the medial segment includes a second movement limiting mechanism configured to limit advancement and retraction of an endoscope attached to a distal end of the distal body portion.

DETAILED DESCRIPTION

The present invention, which may be further understood with reference to the following description and the appended drawings, relates to handle for an apparatus for obtaining tissue samples and, more particularly relates to FNA devices. The handles according to the invention may be used in substantially all procedures employing FNA devices further increasing the efficacy of FNA procedures by improving handling of the device via an ergonomic design and also by permitting rotational movement of the endoscope without the need to rotate the entire shaft of the device. Specifically, presently available devices require that the entire endoscope or the entire handle be rotated in order to affect a rotation of the needle at a target site in the body. The exemplary system and method according to the present invention allows for a selective rotation of only a needle of an FNA device without rotating the entire handle, as will be described in greater detail hereinafter.

Devices and methods according to the present invention comprise an FNA device including an ergonomic handle controlling rotation of an FNA device inserted through the device, the handle being connected to an adjustment portion controlling proximal-distal movement of the FNA needle inserted through the FNA device and through an endoscope attached to a distal portion of the device, the endoscope being configured for insertion into a living body in an operative configuration. Specifically, embodiments of the present invention are directed to a handle configured to control rotation of the FNA needle inserted therethrough while bypassing the need to rotate the entire endoscope, as is customary with presently available devices. It is noted that the use of the term distal herein refers to a direction away from a user and toward a target tissue treatment area and the term proximal refers to a direction approaching a user of the device (e.g., a physician) with a proximal portion of the device remaining external to the patient as an endoscope attached to the distal portion is inserted into the body.

Figure 1:
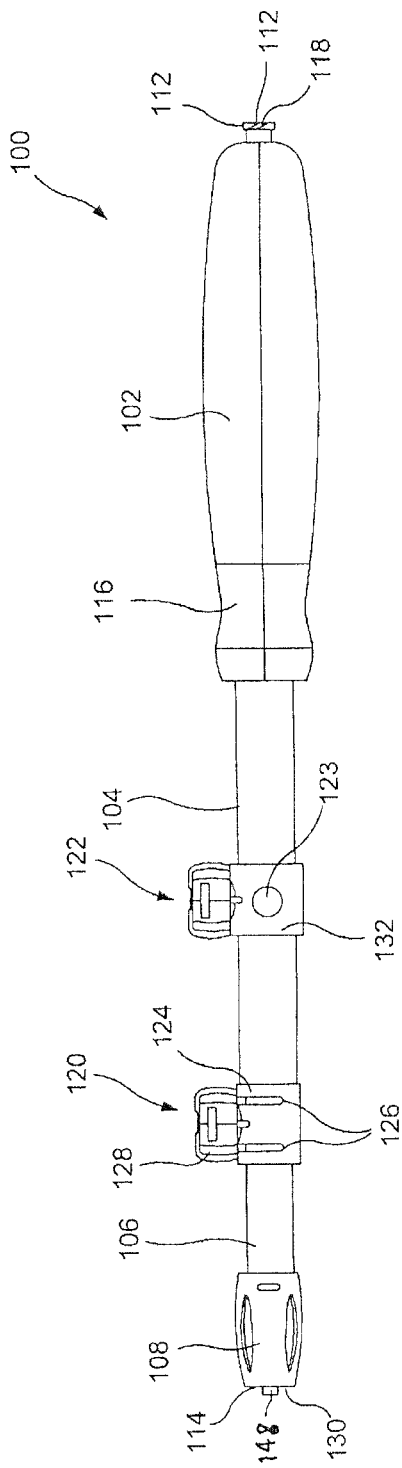
FIG. 1 is a first perspective view of a device according to a first embodiment of the invention.
Figure 2:
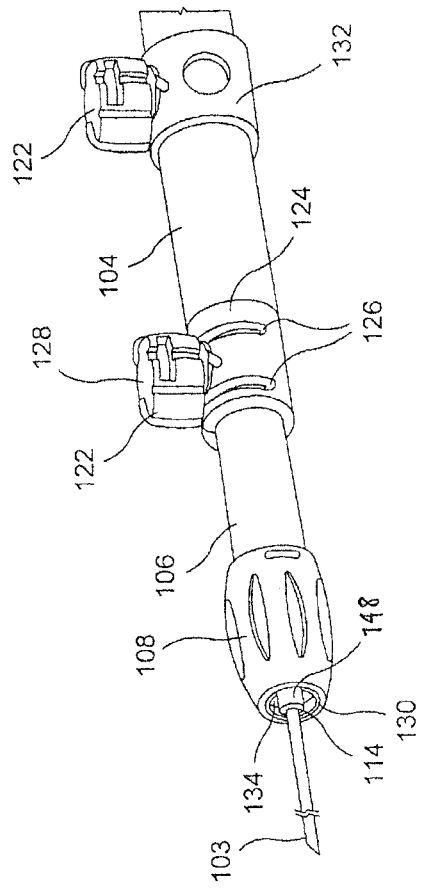
FIG. 2 is a second perspective view of the device of FIG. 1.
Figure 3:
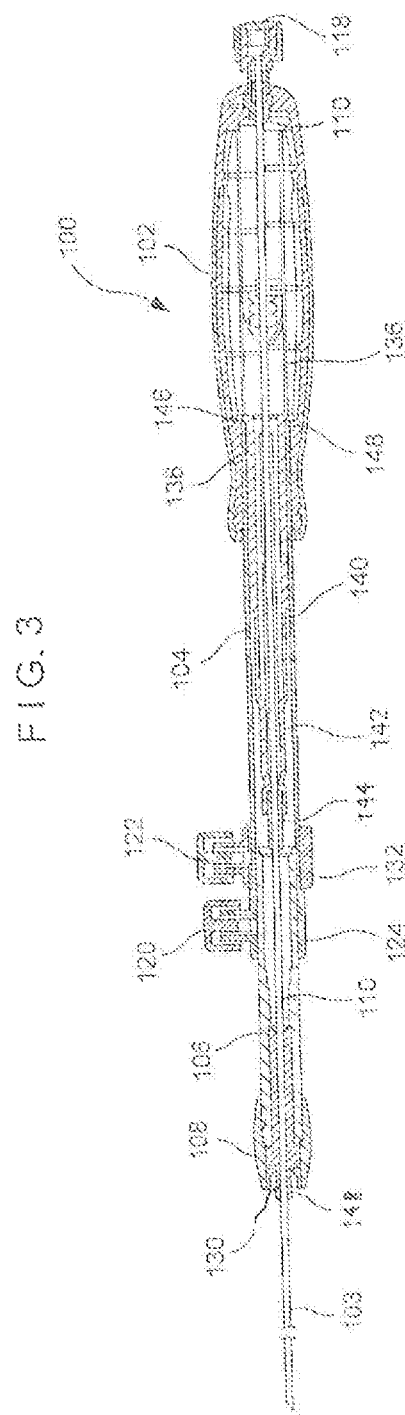
FIG. 3 is a partial cross-sectional view of the device of FIG. 1.
Figure 4:
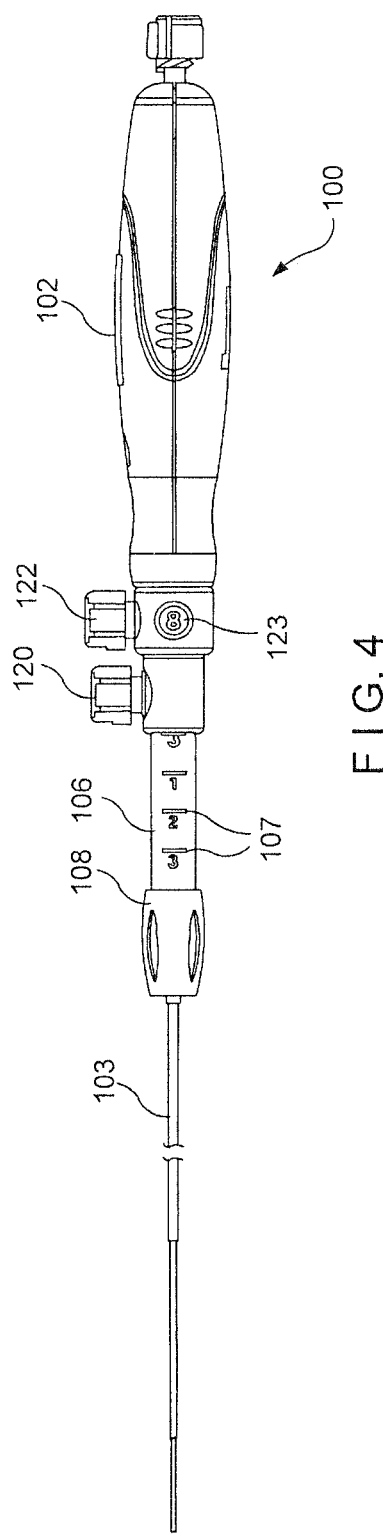
FIG. 4 is a perspective view of the device of FIG. 1 in a first operative configuration.
Figure 5:
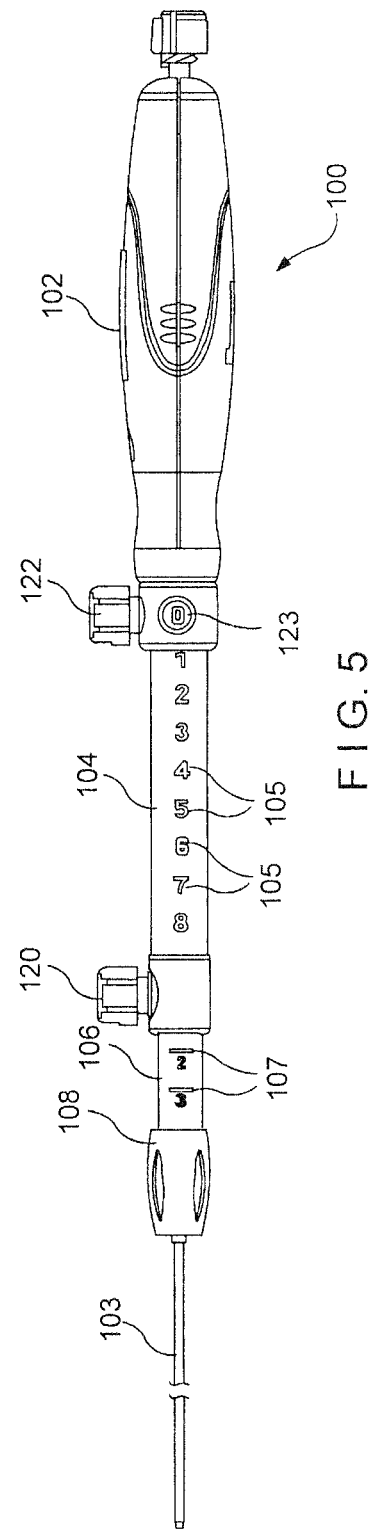
FIG. 5 is a perspective view of the device of FIG. 1 in a second operative configuration.

As shown in FIGS. 1-5, an FNA actuation device 100 according to an exemplary embodiment of the present invention comprises an elongated body having a proximal handle portion 102, a central portion 104, a distal portion 106 and an attachment portion 108 located at a distal end thereof, the attachment portion 108 permitting attachment with an endoscope or other device for insertion into a living body in an operative configuration. In an exemplary embodiment, components of the device 100 may be formed of any combination of a polymer, metal or other known material, as known to those of skill in the art. An exemplary material of the device 100 is selected so that, when attached to an endoscope, the elements are permitted to rotate without breaking or cracking, as will be described in greater detail later on. A lumen 110 extends through the device 100 from a proximal end 112 to a distal end 114. The lumen 110 may be substantially circular in cross-section and may be configured to receive a needle, stylet or another medical device therethrough (e.g., electrodes, knives, pincers, etc.), as those skilled in the art will understand. The needle or other medical device may be configured to reflect ultrasound signals, such as for example, an endoscopic ultrasound ("EUS") needle, as those skilled in the art will understand. It is noted, however, that other cross-sectional shapes of the lumen 110 are also envisioned. Inner walls of a portion of the lumen 110 extending through the proximal handle portion 102 comprise radial abutments or a treated surface (not shown) to permit a frictional or mechanical engagement with an outer wall of a needle 103 to be inserted therethrough. The needle 103 may also comprise an abutment, a recess or a treated surface to permit such an engagement. Thus, when inserted through the lumen 110, the needle 103 may be moved proximally and distally relative to the proximal handle portion 102 by application of a sufficient proximally or distally directed force to a proximal end of the needle but may be prevented from being rotated relative thereto. Rotation of the needle 103 can only be facilitated by a rotation of the proximal handle portion 102. Alternatively, as will be understood by those skilled in the art, the shapes of any portion of the needle, stylet or other medical device and a corresponding portion the lumen 110 may be keyed to one another to prevent relative rotation therebetween. The lumen 110 also extends through the central portion 104 and distal portion 106 but is not rotatably fixed thereto. That is, the lumen 110 is rotatable relative to the central portion 104 and the distal portion 106. Specifically, as shown in FIG. 3, the central portion 104 and distal portion 106 comprise a telescoping internal channel 138 configured with first, second and third sections 140, 142, 144 configured to be retractable into one another upon retraction of one or both of the central and distal portions 104, 106. The lumen 110 extends through the telescoping internal channel 138 and is slidable relative thereto so that retraction and expansion of the telescoping internal channel 138 does not cause proximal or distal movement of the lumen 110. Thus, proximal retraction of the distal portion 106 causes the distal portion 106 to be withdrawn into the central portion 106 and retraction of at least the third section 144 into the second section 142. Similarly, when the central portion 104 is retracted into the proximal handle portion 102, as will be discussed in greater detail later on, the outer wall of the central portion 104 slides into a cavity 136 within the proximal handle portion 102. The lumen 110 is slidable relative to the telescoping internal channel 138 so that proximal retraction of the central portion 104 and distal portion 106 does not proximally retract the needle 103 but rather, permits a greater portion of the needle 103 to be exposed at a distal end of the device 100, as shown in FIG. 4. The telescoping internal channel 138 further comprises a lip 146 formed at a proximal end thereof to permit frictional engagement of the telescoping internal channel 138 with an abutment 148 preventing removal of the central portion 104 from the proximal handle portion 102. The lumen 110 extends proximally from the proximal handle portion 102 by a predetermined distance and comprises an opening 118 opening into the lumen 110 to permit insertion of the needle or other device therethrough.

The proximal handle portion 102 may be substantially cylindrical in shape and may be formed with an outer diameter greater than that of both the central portion 104 and the distal portion 106. It is further noted that the proximal handle portion 102 may also be formed with a non-circular cross-sectional shape without deviating from the scope of the present invention. The proximal handle portion 102 may be formed with a taper so that its diameter increases toward a central portion thereof with proximal and distal ends of the proximal handle portion 102 having a smaller diameter than that of the central portion. The proximal handle portion 102 further comprises an ergonomic groove 116 formed adjacent a distal end thereof to aid in gripping and manipulation thereof. It is noted that although only a single groove 116 is shown, the proximal handle portion 102 may be formed with any number and variety of grooves or abutments configured to aid in ergonomic handling without deviating from the scope of the present invention. The proximal handle portion 102 may also have a soft grip coating (e.g., thermoplastic elastomer) or another surface modification or coating to aid in handling.

The central portion 104 extends distally from the proximal handle portion 102 by a predetermined distance and also has a substantially circular cross-section. A diameter of the central portion 104 in this embodiment may be approximately 13-25 mm. The central portion 104, although securely connected to the proximal handle portion 102, remains rotatable relative thereto. That is, rotation of the proximal handle portion 102 and the lumen 110 does not result in a rotation of the central portion 104. In one embodiment of the invention, the proximal handle portion 102 comprises a radial groove (not shown) formed on an inner wall of a distal rim thereof configured to rotatably engage a radial abutment formed on an outer wall of a proximal rim of the central portion 104. Alternatively, any connection may be forged between the proximal handle portion 102 and the central portion 104 without deviating from the scope of the present invention.

The central portion 104 further comprises a first mechanism 120 and a second mechanism 122 configured to selectively limit a proximal-distal movement of the distal portion 106 relative to the central portion 104 and movement of the central portion 104 relative to the proximal handle portion 102. Specifically, the first mechanism 120 may be formed as a ring 124 extending around a portion of an outer surface of the central portion 104. The ring 124 may be secured to the central portion 104 and may be held in place by a friction fit or any other suitable attachment means known in the art. In an exemplary embodiment, the ring 124 of the first mechanism 120 may be permanently secured to a distal end of the central portion 104. The ring 124 includes a pair of slots 126 extending substantially perpendicular to a longitudinal axis of the central portion 104 and having a length smaller than a circumference of the ring 124. The slots 126 are configured to permit the device to be locked in a desired configuration. Specifically, a profile of an inner surface of the ring 124 adjacent to the outer surface of the distal portion 106 is non-circular (e.g., elliptical) while a knob 128 of the mechanism 120 includes one or more arms (not shown) which extend from a part of the knob 128 which is located between the ring 124 and the outer surface of the distal portion 106. The arms are sized so that, when the knob 128 is rotated to a first orientation, the arms are located within a space formed between a larger diameter portion of the non-circular inner surface of the ring 124 and the distal portion 106 so that the ring 124 is loosely held around the distal portion 106. Rotation of the knob 128 to a second orientation (e.g., by 90° relative to the first orientation) moves the arms into a smaller space between a reduced diameter portion of the non-circular inner surface of the ring 124 and the distal portion 106 so that the ring 124 is pressed tightly against the distal portion 106 locking the positions of the distal portion 106 and the central portion 104.

The distal portion 106 is sized and shaped to be slidably received within the central actuating portion 104 and telescopically extendable therefrom. When the distal portion 106 is manually moved to a desired position (i.e., using markings 107 formed on an outer wall thereof as a guide), the first mechanism 120 is tightened to apply a torque to the distal portion 106 to lock a position thereof. The distal portion 106 also comprises a distal opening 130 through which the distal end 114 of the lumen 110 exits the device 100.

The second mechanism 122 provided over the central portion 104 is formed substantially similarly to the first mechanism 120 but comprises a ring 132 slidable along a length thereof to permit advancement of the central portion 104 into and out of the proximal handle portion 102. Thus, the second mechanism 122 may be positioned over a target portion of the central portion 104 using markings 105 as a guide and tightened to lock a position thereof. In this manner, the second mechanism 122 can be positioned so that only a portion of the central portion 104 located proximally of the second mechanism 122 is retracted into the proximal handle portion 102, as shown in FIG. 4. For example, when the window 123 is positioned over the "8" marker at a distal-most position of the central portion 104, substantially the entire length of the central portion 104 can be withdrawn proximally into the proximal handle portion 102, as shown in FIG. 4. Similarly, when the second mechanism 122 is moved to a proximal-most position along the central portion 104 (i.e., so that a window 123 is positioned over a "0" marker), the central portion 104 is prevented from being retracted into the proximal handle portion 102.

The attachment portion 108 has a greater diameter than the distal portion 106 and comprises internal threading 134 engaging a threaded outer wall of a proximal end of an endoscope (not shown). The distal end 114 of the lumen 110 may be configured so that, when the attachment portion 108 may be coupled to an endoscope, the lumen 110 aligns with and engages a working channel extending through the endoscope (not shown). Specifically, a proximal end of the endoscope (not shown) may be received within the attachment portion 108 and the attachment portion 108 may be rotated to lockingly engage the threads of the endoscope. The distal portion 106 may include an extension member 148 mounted therewithin that is sized and shaped for insertion into the working channel of the endoscope when the attachment portion 108 is coupled to the endoscope. In one embodiment, only the attachment portion 108 may be rotated to threadedly engage the endoscope (not shown). In another embodiment, the attachment portion 108 may not be rotatable relative to the distal portion 106 so that, in order to threadedly engage the endoscope, the entire distal portion 106 must be rotated. In another embodiment of the invention, the attachment portion 108 may be configured to permit a luer lock connection with the endoscope.

In accordance with an exemplary method of the present application, an endoscope may be attached to the attachment portion 108. The central and distal portions 104, 106 are then manipulated to a desired orientation and the first and second mechanisms 120, 122 are tightened to lock the device 100 in the desired configuration. That is, the distal portion 106 may be extended to a length selected such that, when the needle 103 may be inserted into the lumen 110 and through the endoscope, the needle be movable between a first position in which a distal end of the needle may be located within the endoscope lumen (e.g., substantially adjacent a distal end thereof) and a deployed position in which the needle projects distally beyond a distal end of the endoscope by a desired distance. The needle 103 may then be inserted through the FNA device 100 into the working channel of the endoscope until the proximal end of the needle may be locked in position at a proximal end of the device 100. At this point, the device 100 may be configured so that the needle 103 is in the first position with the distal tip thereof received within the endoscope. In addition, at this point, a stylet is preferably placed in a closed configuration in which it seals a distal opening of the needle as the needle is inserted through non-targeted tissue to the target tissue site. The endoscope is then guided to a target location within the body in a conventional manner and a physician or other user determines (e.g., under visual observation via the endoscope) whether a tissue penetrating distal tip of the needle 103 is in a desired orientation relative to target tissue to be sampled. If not, the physician may rotate the proximal handle portion 102 by a desired angle with the rotation being translated only to the lumen 110 and the needle 103 located therein while the central portion 104, distal portion 106 and the entire length of the endoscope remain substantially unaffected by the rotation. The physician freely rotates the needle 103 by any desired angle until the desired orientation is achieved. The needle 103 may then be moved distally out of the endoscope to extend distally therefrom by the desired distance under the guidance of an imaging device, as those skilled in the art will understand. At this point the stylet is also moved to a tissue receiving configuration in which the distal opening of the needle 103 is open to receive tissue. It is further noted that the needle 103 may subsequently be rotated at any point during the target procedure as deemed necessary by the physician.

The present invention has been described with reference to specific exemplary embodiments. Those skilled in the art will understand that various modifications and changes may be made to the embodiments. The specifications are, therefore, to be regarded in an illustrative rather than a restrictive sense.

What is claimed is:

1. A telescoping handle for a medical device, comprising:
   a proximal segment defining a proximal lumen extending longitudinally therethrough, the proximal lumen being sized and shaped to receive an endoscopic medical device therein, the proximal segment including a coupler for coupling the endoscopic medical device thereto so that the endoscopic medical device moves and rotates with the proximal segment;
   a medial segment received within a distal portion of the proximal segment so that the proximal segment is rotatable relative to the medial segment, the medial segment having an outer diameter smaller than an outer diameter of the proximal segment and defining a medial lumen extending therethrough open to the proximal lumen; and
   a distal segment received within a distal portion of the medial segment and defining a distal lumen extending therethrough open to the medial lumen, the distal segment having an outer diameter smaller than an outer diameter of the medial segment,
   wherein the medial segment is telescopically movable into and out of the proximal segment and rotatable relative thereto, the distal segment is telescopically movable into and out of the medial segment, the medial and distal lumens being sized and shaped so that rotation of the proximal segment relative to the medial segment rotates the endoscopic medical device relative to the medial and distal segments and movement of the proximal segment distally over a portion of the medial segment moves the endoscopic medical device axially relative to the medial segment.

2. The telescoping handle of claim 1, further comprising a proximal movement limiting mechanism limiting movement of the medial segment into the proximal segment, the proximal movement limiting mechanism being configured to frictionally engage an outer wall of the medial segment.

3. The telescoping handle of claim 2, further comprising a distal movement limiting mechanism configured to lock a position of the distal segment relative to the medial segment.

4. The telescoping handle of claim 3, wherein the proximal movement limiting mechanism is slidably positioned over a target portion of the medial segment so that only a portion of the medial segment located proximally thereof is retractable into the proximal segment.

5. The telescoping handle of claim 1, wherein the endoscopic medical device is a needle.

6. The telescoping handle of claim 1, wherein the distal segment includes an attachment sized and shaped to engage a corresponding attachment at a proximal end of an endoscope to which the telescoping handle is to be mounted.

7. The telescoping handle of claim 1, wherein the distal segment engages an endoscope via a Luer lock.

8. A telescoping handle for a medical device, comprising:
a proximal segment defining a proximal lumen extending longitudinally therethrough, the proximal lumen being sized and shaped to receive an endoscopic medical device therein, the proximal segment including a coupler for coupling the endoscopic medical device thereto so that the endoscopic medical device moves and rotates with the proximal segment;
a medial segment received within a distal portion of the proximal segment so that the proximal segment is rotatable relative to the medial segment, the medial segment having an outer diameter smaller than an inner diameter of the proximal segment and defining a medial lumen extending therethrough open to the proximal lumen;
a distal segment received within a distal portion of the medial segment and defining a distal lumen extending therethrough open to the medial lumen, the distal segment having an outer diameter smaller than an inner diameter of the medial segment; and
a telescoping internal channel extending through the medial and distal segments, the telescoping channel including first, second and third sections movable relative to one another upon retraction or expansion of the proximal, medial and distal segments relative to one another, wherein the first section is within the proximal segment, the second section is within the medial segment and the third section is within the distal segment;
wherein the medial segment is telescopically movable into and out of the proximal segment and rotatable relative thereto, the distal segment is telescopically movable into and out of the medial segment, the medial and distal lumens being sized and shaped so that rotation of the proximal segment relative to the medial segment rotates the endoscopic medical device relative to the medial and distal segments and movement of the proximal segment distally over a portion of the medial segment moves the endoscopic medical device axially relative to the medial segment.

9. The telescoping handle of claim 8, wherein the medial segment is telescopically movable into and out of the proximal segment and wherein the distal segment is telescopically movable into and out of the medial segment.

10. The telescoping handle of claim 8, wherein the proximal retraction of the distal segment into the medial segment causes retraction of the third section into the second section.

11. The telescoping handle of claim 8, wherein the proximal retraction of the medial segment into the proximal segment causes retraction of the second section into the first section.

12. The telescoping handle of claim 8, wherein the third section has an outer diameter smaller than an inner diameter of the second section.

13. The telescoping handle of claim 11, wherein the second section has an outer diameter smaller than an inner diameter of the first section.

14. The telescoping handle of claim 8, further comprising a proximal movement limiting mechanism limiting movement of the medial segment into the proximal segment, the proximal movement limiting mechanism being configured to frictionally engage an outer wall of the medial segment.

15. The telescoping handle of claim 14, further comprising a distal movement limiting mechanism configured to lock a position of the distal segment relative to the medial segment.

16. The telescoping handle of claim 8, wherein the distal segment includes an attachment sized and shaped to engage a corresponding attachment at a proximal end of an endoscope to which the telescoping handle is to be mounted.

17. The telescoping handle of claim 14, wherein the proximal movement limiting mechanism is slidably positioned over a target portion of the medial segment so that only a portion of the medial segment located proximally thereof is retractable into the proximal segment.

18. The telescoping handle of claim 1, wherein the proximal segment is rotatable relative to the distal segment so that the endoscopic medical device may be rotated within the distal segment without rotating the distal segment relative to an endoscope to which it is coupled.

* * * * *